United States Patent
Maekawa et al.

(10) Patent No.: US 9,829,432 B2
(45) Date of Patent: Nov. 28, 2017

(54) GAS MEASURING APPARATUS

(71) Applicant: Kabushiki Kaisha Toshiba, Minato-ku (JP)

(72) Inventors: Akira Maekawa, Kamakura (JP); Miyuki Kusaba, Meguro (JP); Shigeyuki Takagi, Fujisawa (JP); Hiroshi Hasegawa, Yokosuka (JP); Tsutomu Kakuno, Fujisawa (JP); Yasutomo Shiomi, Koza (JP)

(73) Assignee: Kabushiki Kaisha Toshiba, Minato-ku (JP)

(*) Notice: Subject to any disclaimer, the term of this patent is extended or adjusted under 35 U.S.C. 154(b) by 0 days.

(21) Appl. No.: 15/260,651

(22) Filed: Sep. 9, 2016

(65) Prior Publication Data
US 2016/0377534 A1    Dec. 29, 2016

Related U.S. Application Data

(63) Continuation of application No. PCT/JP2015/057700, filed on Mar. 16, 2015.

(30) Foreign Application Priority Data

Sep. 22, 2014 (JP) ................. 2014-192322

(51) Int. Cl.
*G01J 5/02* (2006.01)
*G01N 21/3504* (2014.01)
(Continued)

(52) U.S. Cl.
CPC ........... *G01N 21/3504* (2013.01); *A61B 5/00* (2013.01); *A61B 5/0059* (2013.01); *A61B 5/082* (2013.01);
(Continued)

(58) Field of Classification Search
CPC .............. G01N 21/3504; G01N 21/39; G01N 2800/085
See application file for complete search history.

(56) References Cited

U.S. PATENT DOCUMENTS 5,770,793 A * 6/1998 Stock ................. G01N 21/3504
250/343
5,964,712 A * 10/1999 Kubo ..................... A61B 5/097
422/413
(Continued)

FOREIGN PATENT DOCUMENTS

JP    59-197837 A    11/1984
JP    10-197444 A    7/1998
(Continued)

OTHER PUBLICATIONS

Sturm et al., "Eddy covariance measurements of CO2 isotopologues with a quantum cascade laser absorption spectrometer," 2012, Agricultural and Forest Meteorology, vol. 152, pp. 73-82.*
(Continued)

*Primary Examiner* — Kiho Kim
(74) *Attorney, Agent, or Firm* — Oblon, McClelland, Maier & Neustadt, L.L.P.

(57) ABSTRACT

A gas measuring apparatus includes a cell portion, a light source portion, a detection portion, and a control portion. The cell portion includes a space into which a sample gas containing breath containing a first isotope of carbon dioxide and a second isotope of carbon dioxide is introduced. The light source portion changes a wavelength of the light in a band of 4.345 μm or more and 4.384 μm or less. The detection portion performs an operation including first detection of an intensity of the light passing through the space and second detection of an intensity of the light passing through the space into which the sample gas is not introduced. The control portion calculates a ratio of an
(Continued)

amount of the second isotope to an amount of the first isotope based on a result of the first detection and a result of the second detection.

7 Claims, 8 Drawing Sheets

(51) Int. Cl.
| | |
|---|---|
| G01N 21/39 | (2006.01) |
| G01N 33/497 | (2006.01) |
| H01S 5/343 | (2006.01) |
| G01N 21/05 | (2006.01) |
| H01S 5/125 | (2006.01) |
| H01S 5/34 | (2006.01) |
| A61B 5/00 | (2006.01) |
| A61B 5/08 | (2006.01) |
| G01N 33/00 | (2006.01) |

(52) U.S. Cl.
CPC ............. *G01N 21/05* (2013.01); *G01N 21/39* (2013.01); *G01N 33/497* (2013.01); *H01S 5/125* (2013.01); *H01S 5/3401* (2013.01); *H01S 5/343* (2013.01); *H01S 5/34313* (2013.01); *H01S 5/34346* (2013.01); *G01N 33/004* (2013.01); *G01N 2021/399* (2013.01); *G01N 2201/12* (2013.01)

(56) References Cited

U.S. PATENT DOCUMENTS

| | | | | |
|---|---|---|---|---|
| 6,599,253 B1* | 7/2003 | Baum | ................... | A61B 5/0813 356/303 |
| 7,063,667 B1* | 6/2006 | Ben-Oren | ............ | A61B 5/0836 422/84 |
| 2011/0270113 A1* | 11/2011 | Heyne | ................... | A61B 5/0836 600/531 |

FOREIGN PATENT DOCUMENTS

| | | |
|---|---|---|
| JP | 2000-097854 A | 4/2000 |
| JP | 2000-97854 A | 4/2000 |
| JP | 2001-324446 A | 11/2001 |
| JP | 2002-340795 A | 11/2002 |
| JP | 2002-350340 A | 12/2002 |
| JP | 2003-232732 A | 8/2003 |
| JP | 2005-106546 A | 4/2005 |
| JP | 2010-509586 A | 3/2010 |
| JP | 2011-512532 A | 4/2011 |
| JP | 2013-515950 | 5/2013 |
| JP | 5797665 B2 | 10/2015 |
| WO | WO 2007/088885 A1 | 8/2007 |

OTHER PUBLICATIONS

Nagali et al., "Design of a diode-laser sensor to monitor water vapor in high-pressure combustion gases," Dec. 20, 1997, Applied Optices, vol. 36, No. 36, pp. 9518-9527.*

International Search Report and Written Opinion dated May 26, 2016, in PCT/292015/05770—with partial English translation.

Worle, et al.; "Breath Analysis with Broadly Tunable Quantum Cascade Lasers", Analytical Chemistry, Jan. 15, 2013, vol. 85, p. 2697-2702.

Kasyutich, et al., "13Co2/12Co2 isotopic ratio measurements with a continuous-wave quantum cascade laser in exhaled breath", Infrared Physics & Technology, Jan. 2012, vol. 55, No. 1, p. 60-66.

Stepanov, E. V., "Laser analysis of the 13C/12C isotope ratio in Co2 in exhaled air", Quantum Electronics, Nov. 2002, vol. 32, No. 11, p. 981-986.

Kasyutich, et al., "13Co2/12Co2 isotopic ratio measurements with a continuous-wave quantum cascade laser in exhaled breath", Infrared Physics & Technology, Jan. 2012, vol. 55, No. 1, p. 60-66 (reference previously filed, submitting Statement of Relevancy only).

Stepanov, E. V., "Laser analysis of the 13C/12C isotope ratio in Co2 in exhaled air", Quantum Electronics, Nov. 2002, vol. 32, No. 11, p. 981-986 (reference previously filed, submitting Statement of Relevancy only).

Worle, et al.; "Breath Analysis with Broadly Tunable Quantum Cascade Lasers", Analytical Chemistry, Jan. 15, 2013, vol. 85, p. 2697-2702 (reference previously filed, submitting Statement of Relevancy only).

* cited by examiner

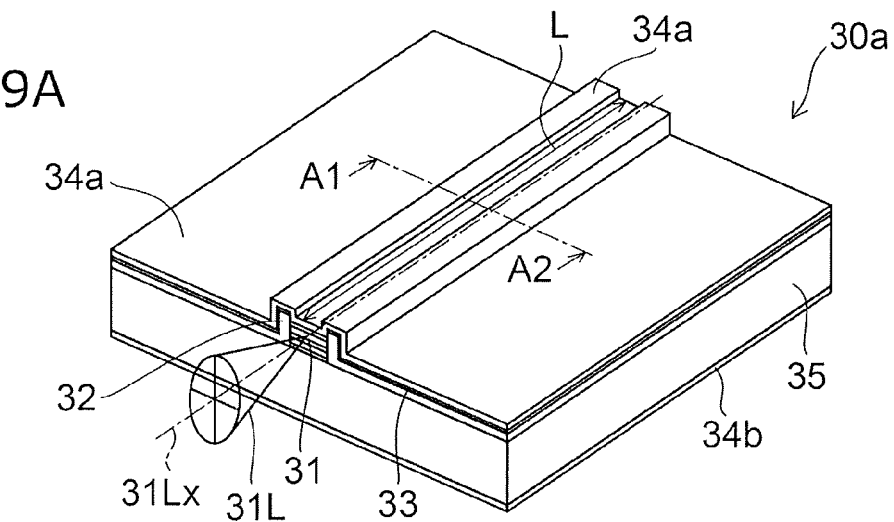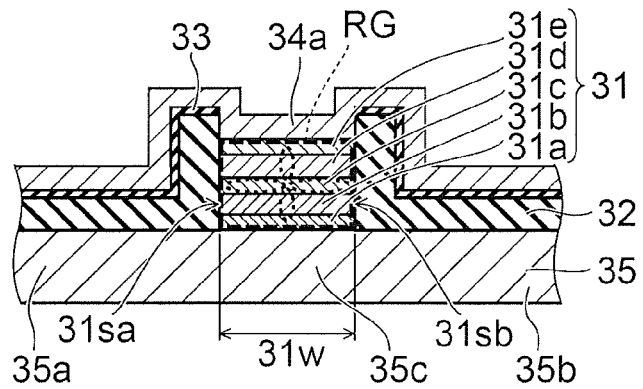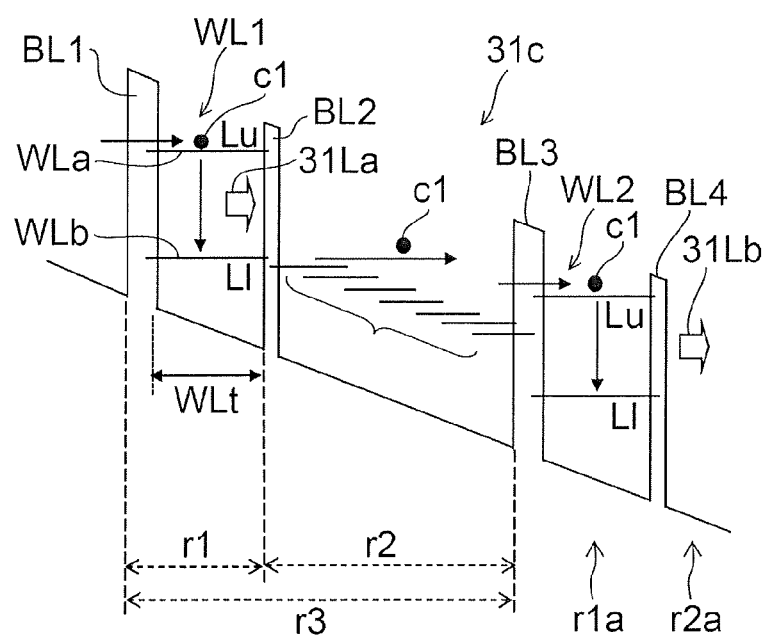

US 9,829,432 B2

GAS MEASURING APPARATUS

CROSS-REFERENCE TO RELATED APPLICATIONS

This is a continuation application of International Application PCT/JP2015/057700, filed on Mar. 16, 2015. This application also claims priority to Japanese Application No. 2014-192322, filed on Sep. 22, 2014. The entire contents of each are incorporated herein by reference.

FIELD

This invention relates to a gas measuring apparatus.

BACKGROUND

The gas measuring apparatus includes a breath diagnostic apparatus and so on. In a breath diagnostic apparatus, a breath gas is measured. Based on the result of this measurement, prevention and early detection of diseases are facilitated. In the breath diagnostic apparatus, it has been desired to obtain high-precision measurement results.

BRIEF DESCRIPTION OF THE DRAWINGS

FIGS. 9A to 9C are schematic views illustrating a part of the breath diagnostic apparatus according to the embodiment.

DETAILED DESCRIPTION

In general, according to one embodiment, a gas measuring apparatus includes a cell portion, a light source portion, a detection portion, and a control portion. The cell portion includes a space into which a sample gas containing a first isotope of carbon dioxide and a second isotope of carbon dioxide is introduced. The light source portion allows light to enter the space and changes a wavelength of the light in a wavelength band of 4.345 μm or more and 4.384 μm or less. The wavelength band includes at least a first wavelength corresponding to one of absorption peak of the first isotope and a second wavelength corresponding to one of absorption peak of the second isotope. The detection portion performs an operation including first detection of an intensity of the light passing through the space into which the sample gas is introduced and second detection of an intensity of the light passing through the space into which the sample gas is not introduced. The control portion calculates a ratio of an amount of the second isotope to an amount of the first isotope in the sample gas based on a result of the first detection and a result of the second detection.

Embodiments of the invention will be described hereinafter with reference to the accompanying drawings.

The figures are schematic or conceptual, and a relationship between the thickness and width in each component, a ratio of size between components may not necessarily be same as the actual configuration. Furthermore, even when representing the same component, the dimension and ratio may be represented differently in different figures. In the specification and the figures of the application, the same reference numbers are applied to the same elements already described in relation to previous figures, and detailed description will not be repeated as appropriate.

First Embodiment

Figure 1:
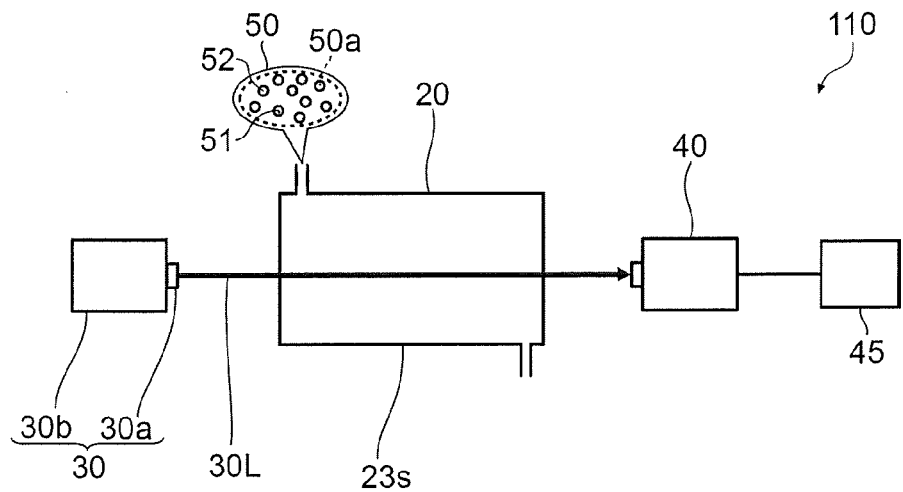
FIG. 1 is a schematic view illustrating a breath diagnostic apparatus according to a first embodiment.

FIG. 1 is a schematic view illustrating a breath diagnostic apparatus according to a first embodiment.

As shown in FIG. 1, a breath diagnostic apparatus 110 according to the embodiment includes a cell portion 20, a light source portion 30, a detection portion 40, and a control portion 45.

Into the cell portion 20, a sample gas 50 is introduced. That is, into a space 23s provided in the cell portion 20, the sample gas 50a is introduced. The sample gas 50 contains breath 50a. The breath 50a is, for example, breath of an animal including a human being. In the breath 50a, first carbon dioxide 51 (first isotope) containing $^{12}C$ and second carbon dioxide 52 (second isotope) containing $^{13}C$. The first carbon dioxide 51 is $^{12}CO_2$. The second carbon dioxide 52 is $^{13}CO_2$. In these carbon dioxide species, an isotope of oxygen may be contained.

As will be described later, diagnosis can be made by obtaining a relative ratio of $^{13}CO_2$ to $^{12}CO_2$ contained in the breath 50a. For example, a person takes a labeled compound with enriched $^{13}C$ ($^{13}C$-labeled compound). The breath 50a at this time is evaluated.

As will be described later, the light absorption of the first carbon dioxide 51 has a first peak at a first wavelength. The light absorption of the second carbon dioxide 52 has a second peak at a second wavelength. By using light with wavelengths corresponding to the wavelengths of these two peaks, the amounts (a relative ratio) of the first carbon dioxide 51 and the second carbon dioxide 52 can be detected.

The light source portion 30 allows light (measurement light 30L) to enter the space 23s. The light source portion 30 changes the wavelength of the light (measurement light 30L). The wavelength is changed in a specific wavelength band. For example, the wavelength of the light is changed in a wavelength band of 4.34 μm or more and 4.39 μm or less. This wavelength band includes the first wavelength of the first peak of the light absorption of the first carbon dioxide 51 and the second wavelength of the second peak of the light absorption of the second carbon dioxide 52.

In this example, the light source portion 30 includes a light-emitting portion 30a and a driving portion 30b. The driving portion 30b is electrically connected to the light-emitting portion 30a. The driving portion 30b supplies electric power for light emission to the light-emitting portion 30a. As will be described later, as the light-emitting portion 30a, for example, a distributed feedback (DFB) quantum cascade laser is used. As the light-emitting portion 30a, an interband cascade laser (ICL) may be used.

In the light source portion 30, the change in the wavelength is performed in a short time (for example, about 100 ms or less). For example, a center value of the wavelength of the measurement light 30L is 4.34 µm or more and 4.39 µm or less. The wavenumber is 2278 cm$^{-1}$ or more and 2304 cm$^{-1}$ or less. The width of the change in the wavenumber in the wavelength band WL is, for example, about 1 cm$^{-1}$.

The measurement light 30L passes through the space 23s of the cell portion 20. A part of the measurement light 30L is absorbed by substances (the first carbon dioxide 51 and the second carbon dioxide 52) contained in the sample gas 50. Components with a wavelength specific to these substances in the measurement light 30L are absorbed. The degree of absorption depends on the concentration of the substance.

The detection portion 40 detects the measurement light 30L passing through the space 23s, for example, in a state where the sample gas 50 is introduced into the space 23s. The detection portion 40 detects the intensity of light (measurement light 30L) passing through the space 23s. As the detection portion 40, an element having sensitivity to an infrared region is used. As the detection portion 40, for example, a thermopile or a semiconductor sensor element (for example, an MCT (HgCdTe)), or the like is used. In the embodiment, the detection portion 40 is arbitrary.

The detection portion 40 detects not only the intensity of light when the sample gas 50 is introduced into the space 23s, but also the intensity of light when the sample gas 50 is not introduced into the space 23s. The latter is used as a reference value in the detection. That is, the detection portion 40 performs first detection of the intensity of light (measurement light 30L) passing through the space 23s into which the sample gas 50 is introduced, and second detection of the intensity of light (measurement light 30L) passing through the space 23s into which the sample gas 50 is not introduced.

The control portion 45 calculates the ratio of the amount of the second carbon dioxide 52 (second isotope) to the amount of the first carbon dioxide 51 (first isotope) in the sample gas based on the result of the first detection and the result of the second detection.

In the embodiment, a high-precision breath diagnosis can be made.

In the embodiment, the above-mentioned detection may be performed a plurality of times. That is, the detection portion 40 performs the operation including the first detection of the intensity of the light (measurement light 30L) passing through the space 23s into which the sample gas 50 is introduced and the second detection of the intensity of the light (measurement light 30L) passing through the space 23s into which the sample gas 50 is not introduced a plurality of times. At this time, the control portion 45 calculates the ratio of the amount of the second carbon dioxide 52 to the amount of the first carbon dioxide 51 in the sample gas 50 based on the results obtained by the above-mentioned operation performed a plurality of times. That is, the ratio of the amount of the second carbon dioxide 52 to the amount of the first carbon dioxide 51 is calculated based on a plurality of first detection results obtained by the above-mentioned operation performed a plurality of times and a plurality of second detection results obtained by the above-mentioned operation performed a plurality of times.

By doing this, a higher-precision breath diagnosis can be made.

Further, in carbon dioxide containing isotopes of carbon, the ratio of $^{13}CO_2$ to $^{12}CO_2$ is about 1% or so. Then, it is not easy to measure the relative amount of $^{13}CO_2$ in such a minute amount with high precision. In view of this, a special configuration capable of measuring the relative amount of $^{13}CO_2$ with high precision has been desired.

For example, there is a method in which collected breath is once stored in a given container or the like, and the breath stored in the container is analyzed. In this method, breath exhaled by a person or the like is once stored in a container, and therefore, the measurement result may sometimes be affected by, for example, a variation in the container or the like. Due to this, it is difficult to sufficiently increase the stability of detection.

On the other hand, in the embodiment, breath exhaled by a person or the like is introduced into the space 23s of the cell portion 20 without being stored in a container or the like. Therefore, it is not affected by a variation in another member such as a container, and thus, the stability of the detection result is high.

Further, the intensity of absorption of $^{13}CO_2$ and the intensity of absorption of $^{12}CO_2$ are largely different. Therefore, there is a reference example in which a cell for detecting $^{13}CO_2$ and a cell for detecting $^{12}CO_2$ are provided separately. However, in this method, detection is performed using different cells, and therefore, different samples are evaluated. Due to this, the stability of detection cannot be sufficiently increased. Further, in the case where a plurality of cells is provided, a detector is provided for each cell. In the plurality of detectors, the surrounding environment (for example, temperature) or temperature drift has a large effect. For example, the drift of sensitivity (and output) varies among the plurality of detectors, and the precision of the measurement results is decreased. In particular, the measurement light 30L is located in the infrared region, and therefore is largely affected by a temperature.

On the other hand, in the embodiment, the absorption intensities of both $^{13}CO_2$ and $^{12}CO_2$ are detected in one space 23s (one cell portion 20). The absorption intensities of both are detected by one detector (detection portion 40). Then, in the light source portion 30, by changing the wavelength in a specific wavelength band, the absorption intensities of both $^{13}CO_2$ and $^{12}CO_2$ are detected at substantially the same timing. Therefore, the stability of the detection results is high. In the embodiment, the effect of the surrounding environment or temperature drift can be suppressed, and high precision is obtained.

Further, in the embodiment, the change in the wavelength can be performed in a relatively short time. Due to this, detection is performed a plurality of times for the same sample. By averaging (integrating) the results of detection performed a plurality of times, high-precision detection can be performed.

In the embodiment, by using one cell portion 20, the absorption intensities of both $^{13}CO_2$ and $^{12}CO_2$ are detected. Therefore, the apparatus can be miniaturized as compared with the reference example using a plurality of cells.

Figure 2A:
FIGS. 2A to 2C are schematic views illustrating the breath diagnostic apparatus according to the first embodiment.
Figure 2B:
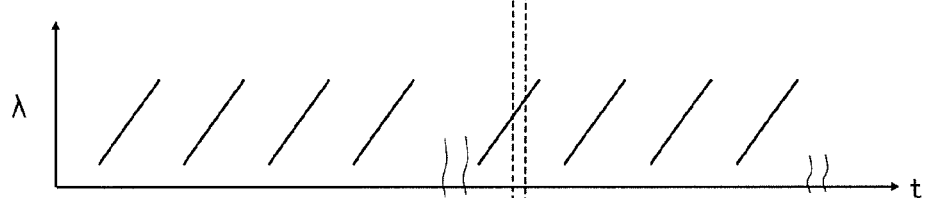
Figure 2C:
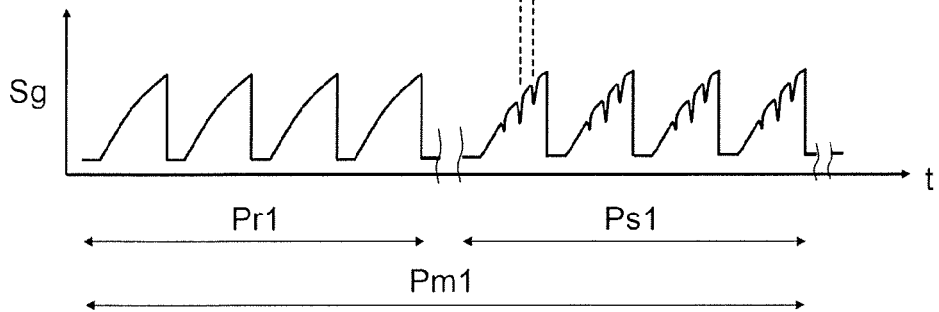

FIGS. 2A to 2C are schematic views illustrating the breath diagnostic apparatus according to the first embodiment.

FIG. 2A shows an example of a change in a current Is that controls the measurement light 30L emitted from the light source portion 30. The current Is may be a current supplied to the light-emitting portion 30a. FIG. 2B shows an example of a change in the wavelength of the measurement light 30L emitted from the light source portion 30. FIG. 2C shows an example of a change in a signal detected by the detection portion 40. In these drawings, the horizontal axis represents a time t. The vertical axis in FIG. 2A represents a current Is. The vertical axis in FIG. 2B represents a wavelength λ. The vertical axis in FIG. 2C represents a signal intensity Sg.

As shown in these drawings, a reference data measurement period Pr1 and a sample data measurement period Ps1 are provided. In the reference data measurement period Pr1, the sample gas 50 is not introduced into the space 23s. In the sample data measurement period Ps1, the sample gas 50 is introduced into the space 23s.

In the reference data measurement period Pr1, the wavelength of the measurement light 30L emitted from the light source portion 30 is changed. This change is repeatedly performed a plurality of times. The intensity of this measurement light 30L is detected by the detection portion 40. In the detection portion 40, the signal intensity Sg is detected a plurality of times.

In the sample data measurement period Ps1, the sample gas 50 is introduced into the space 23s, and a part of the measurement light 30L is absorbed by the first carbon dioxide 51 and the second carbon dioxide 52. For example, at a first wavelength λ1 corresponding to an absorption peak of the first carbon dioxide 51, the signal intensity Sg decreases. For example, at a second wavelength λ2 corresponding to an absorption peak of the second carbon dioxide 52, the signal intensity Sg decreases.

By comparing the signal intensity Sg in the reference data measurement period Pr1 (reference intensity) with the signal intensity Sg in the sample data measurement period Ps1 (sample intensity), a value corresponding to the amount of the first carbon dioxide 51 and a value corresponding to the amount of the second carbon dioxide 52 are obtained. For example, a ratio of the sample intensity to the reference intensity is obtained. For example, a difference between the reference intensity and the sample intensity is obtained. By doing this, a value corresponding to the amount of the first carbon dioxide 51 and a value corresponding to the amount of the second carbon dioxide 52 are obtained. A ratio of the amount of the second carbon dioxide 52 to the amount of the first carbon dioxide 51 is obtained.

In at least one reference data measurement period Pr1 and at least one sample data measurement period Ps1, one measurement (calculation of the ratio of the amount of the second carbon dioxide 52 to the amount of the first carbon dioxide 51) is performed. That is, one measurement period Pm1 includes at least one reference data measurement period Pr1 and at least one sample data measurement period Ps1.

Figure 3A:
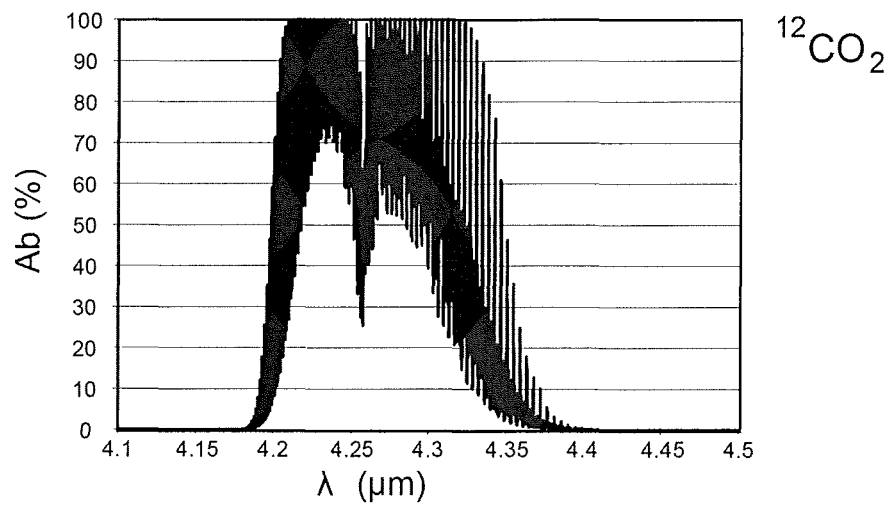
FIGS. 3A and 3B are graphs illustrating the characteristics of carbon dioxide.
Figure 3B:
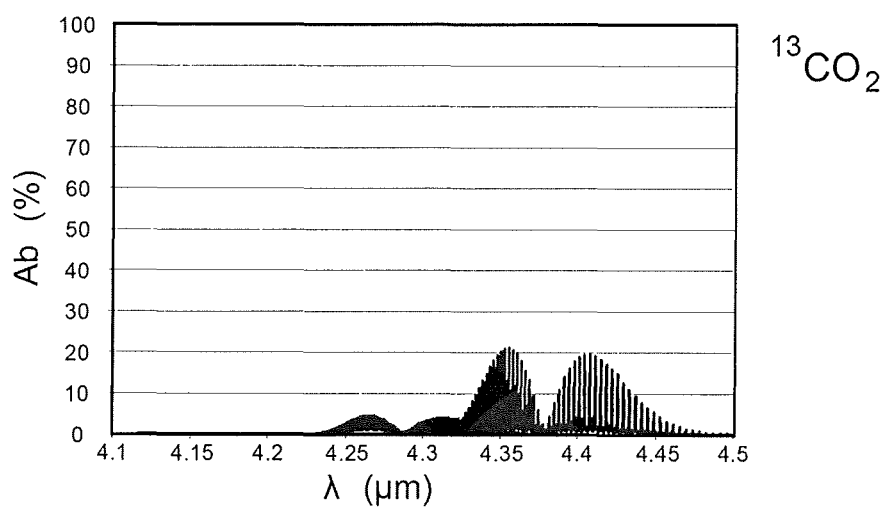

FIGS. 3A and 3B are graphs illustrating the characteristics of carbon dioxide.

Figure 4A:
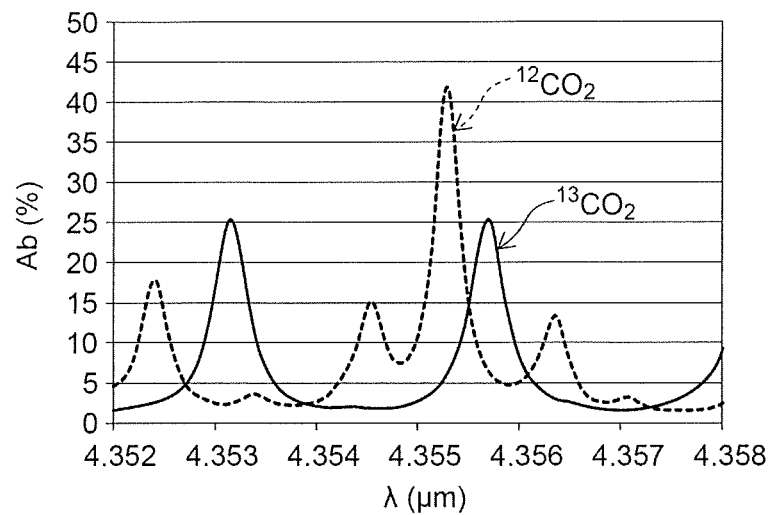
FIGS. 4A and 4B are graphs illustrating the characteristics of carbon dioxide.
Figure 4B:
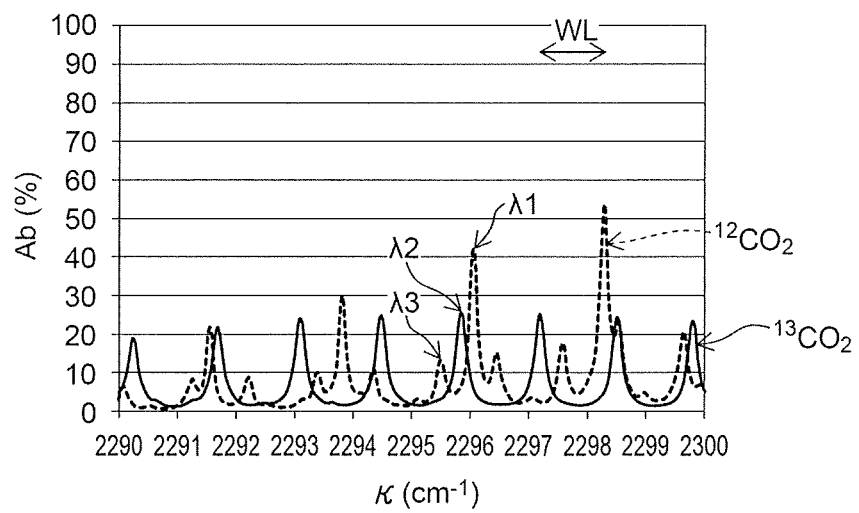

FIGS. 4A and 4B are graphs illustrating the characteristics of carbon dioxide.

FIG. 3A shows an absorption spectrum of $^{12}CO_2$, and FIG. 3B shows an absorption spectrum of $^{13}CO_2$. In these drawings, the optical path lengths are the same. FIG. 4A shows the absorption spectra of $^{12}CO_2$ and $^{13}CO_2$ by expanding the wavelength. FIG. 4B shows the absorption spectra by expanding the wavenumber. The horizontal axis of each of FIGS. 3A, 3B, and 4A represents the wavelength λ (μm). The horizontal axis of FIG. 4B represents the wavenumber κ ($cm^{-1}$). The vertical axis represents the absorption ratio Ab (%).

As shown in FIGS. 3A, 3B, 4A, and 4B, each of $^{12}CO_2$ and $^{13}CO_2$ has an intrinsic absorption. As shown in FIG. 4B, for example, the first wavelength λ1 (wavenumber) corresponding to one absorption peak of $^{12}CO_2$ is, for example, 2296.06 $cm^{-1}$. For example, the second wavelength λ2 (wavenumber) corresponding to one absorption peak of $^{13}CO_2$ is, for example, 2295.85 $cm^{-1}$. Further, as a third wavelength λ3 (wavenumber) corresponding to another absorption peak of $^{12}CO_2$, a peak at 2295.50 $cm^{-1}$ is present.

For example, the wavelength of the measurement light 30L emitted from the light source portion 30 is changed (swept) in a wavelength band WL. The wavelength band WL includes the first wavelength λ1 and the second wavelength λ2. The wavelength band WL preferably further includes at least either of another absorption peak of $^{12}CO_2$ and another absorption peak of $^{13}CO_2$.

The range of the wavelength band WL (the range of the wavenumber band) is, for example, about 1 $cm^{-1}$.

The wavelength band WL is determined so as to obtain the absorption intensity of $^{13}CO_2$ relatively close to the absorption intensity of $^{12}CO_2$. According to this, it is possible to detect the amounts of these carbon dioxide species with high precision.

As described above, the width of the change in the wavelength (wavelength band WL) emitted from the light source portion 30 is about 1 $cm^{-1}$. The number of absorption peaks of carbon dioxide in the range of the wavelength band WL is more preferably 3 or more. That is, the wavelength band WL includes the first wavelength of the first peak of the light absorption of the first carbon dioxide, the second wavelength of the second peak of the light absorption of the second carbon dioxide, and the third wavelength of the third peak of the light absorption of the first carbon dioxide or the light absorption of the second carbon dioxide. The third wavelength is, for example, between the first wavelength and the second wavelength. By performing curve fitting using the measurement results of three or more absorption peaks, it becomes possible to perform detection with higher precision.

In the range of the wavelength band WL, a plurality of absorption peaks of $^{13}CO_2$ may be present. By calculating the concentration of $^{13}CO_2$ based on the change in the signal (intensity Sg) at the wavelength of a plurality of peaks, it becomes possible to perform detection with higher precision.

For example, the wavelength band WL includes 2296.06 $cm^{-1}$ corresponding to an absorption peak of $^{12}CO_2$ and 2295.85 $cm^{-1}$ corresponding to an absorption peak of $^{13}CO_2$. The wavelength band WL further includes 2295.50 $cm^{-1}$ corresponding to an absorption peak of $^{12}CO_2$.

The existing ratio of $^{12}CO_2$ is about 98%. On the other hand, the existing ratio of $^{13}CO_2$ is about 1%. In the embodiment, it is preferred that the absorption ratio of the absorption peak at the existing ratio of $^{13}CO_2$ is substantially the same as the absorption ratio of the absorption peak at the existing ratio of $^{12}CO_2$. According to this, it becomes easy to detect the absorption of these isotopes by one light source portion 30 and one detection portion 40.

In the embodiment, for example, the absorption of $^{12}CO_2$ at the wavelength of the absorption peak of $^{13}CO_2$ corresponds to a non-peak. At this time, it is preferred that the absorption ratio of the absorption peak of $^{13}CO_2$ at this wavelength is higher than the absorption ratio of $^{12}CO_2$ (the absorption ratio at a non-peak of $^{12}CO_2$) at this wavelength.

On the other hand, the range of the wavenumber in the wavelength band WL swept when using a DFB quantum cascade laser is about 1 $cm^{-1}$. For example, in the range of this wavelength band WL, an absorption peak of $^{12}CO_2$ and an absorption peak of $^{13}CO_2$ are present. The measurement is performed using light having the wavelength band WL. According to this, it becomes possible to perform measurement with high speed and high sensitivity using a DFB quantum cascade laser.

Further, it is preferred that in the range of the wavenumber (about 1 $cm^{-1}$) in the wavelength band WL, the following three absorption peaks: one absorption peak of $^{12}CO_2$, one absorption peak of $^{13}CO_2$, and one absorption peak of either of $^{12}CO_2$ and $^{13}CO_2$ are present. According to this, it becomes possible to perform high-precision detection by curve fitting.

That is, for example, when the isotope ratio is obtained, an absorption spectrum obtained by measurement and a spectrum (for example, a theoretical spectrum) to serve as a standard are fitted. For example, as previously described with respect to FIGS. 2(a) to 2(c), a wavelength (that is, a wavenumber) is determined based on a time t. For example, first, a time-absorption coefficient characteristic curve obtained by measurement is converted to a wavenumber-absorption coefficient characteristic curve. Then, this characteristic obtained by conversion is fitted to a characteristic curve of a spectrum (for example, a theoretical spectrum) to serve as a standard.

At this time, the time-current characteristic illustrated in FIG. 2(a) is known (a preset sawtooth wave), however, the current-wavelength characteristic depends on the quantum cascade laser characteristic. According to the study made by the inventor, this current-wavelength characteristic was found to be precise when it was assumed to be a characteristic of not a linear, but quadratic function. Therefore, the time-wavenumber characteristic is a quadratic function.

For example, three or more absorption peaks are obtained, and based on the wavenumbers corresponding to the times of the respective peaks, coefficients (three coefficients) of a time-wavenumber conversion formula are obtained. By doing this, the fitting precision can be improved.

In the embodiment, in the range of the wavenumber (about 1 cm$^{-1}$) in the wavelength band WL, three or more absorption peaks are present. Due to this, it becomes possible to perform high-precision detection by curve fitting.

That is, in the embodiment, the wavenumber in the wavelength band WL is set to 2281 cm$^{-1}$ or more and 2301 cm$^{-1}$ or less. That is, the wavelength in the wavelength band WL is set to 4.345 μm or more and 4.384 μm or less. According to this, the above-mentioned conditions can be satisfied.

Figure 5A:
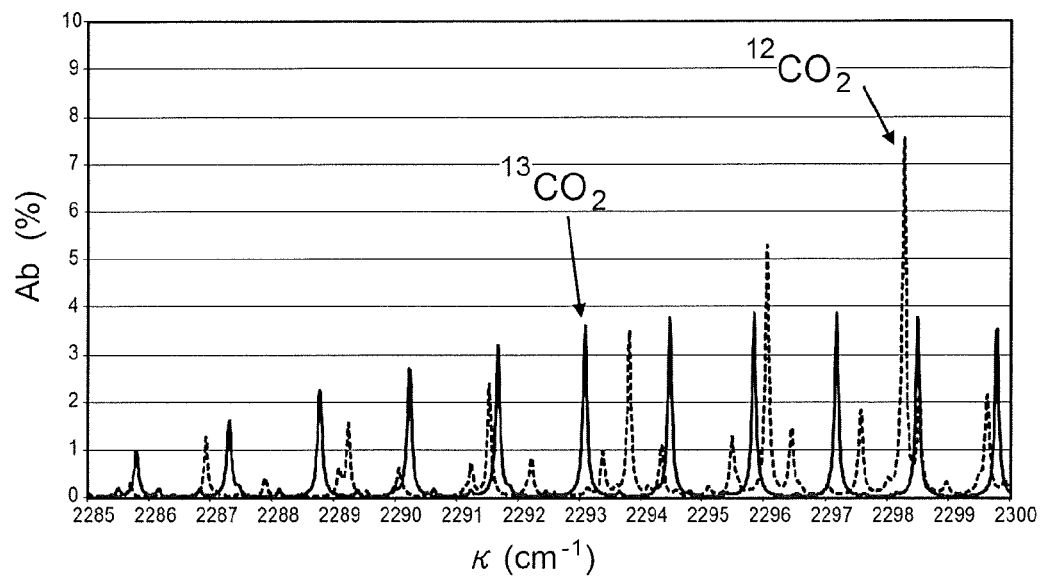
FIGS. 5A and 5B are graphs illustrating the characteristics of carbon dioxide.
Figure 5B:
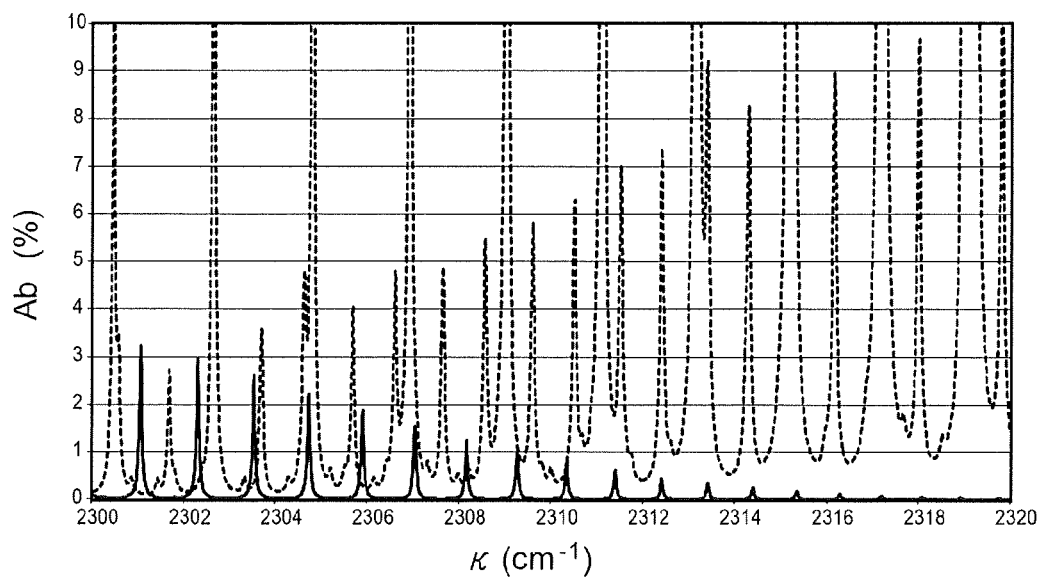

FIGS. 5A and 5B are graphs illustrating the characteristics of carbon dioxide.

These graphs show absorption spectra of $^2CO_2$ and $^{13}CO_2$.

The wavelength band WL is appropriately determined according to the absorption spectrum of carbon dioxide. It is preferred that in the wavelength band WL, the intensity of the absorption peak of $^{13}CO_2$ is higher than the intensity of the non-peak of $^{12}CO_2$.

Figure 6:
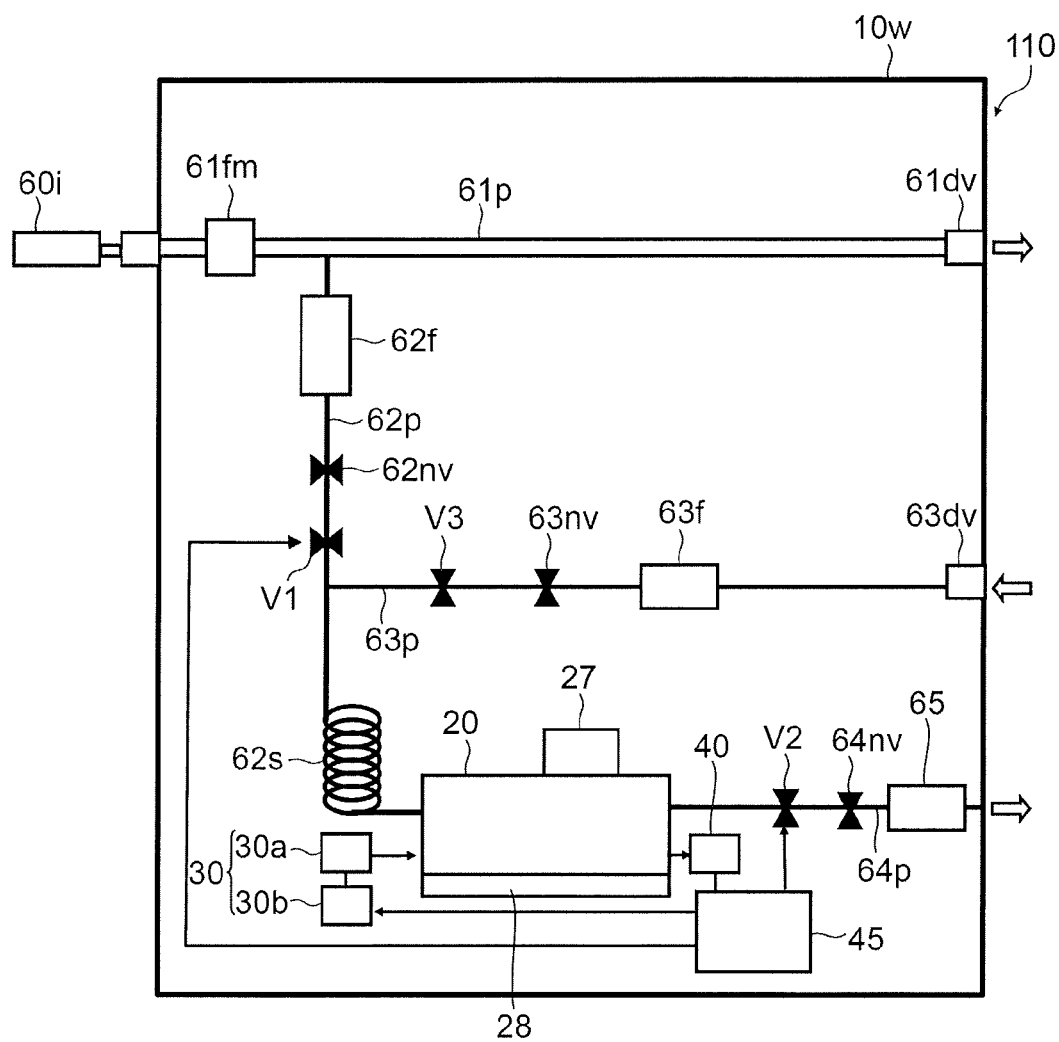
FIG. 6 is a schematic view illustrating the breath diagnostic apparatus according to the first embodiment.

FIG. 6 is a schematic view illustrating the breath diagnostic apparatus according to the first embodiment.

As shown in FIG. 6, in the breath diagnostic apparatus 110, a housing 10w is provided. In the housing 10w, the cell portion 20, the light source portion 30, the detection portion 40, and the control portion 45 are provided. The control portion 45 may be provided outside the housing 10w.

A gas introduction portion 60i is connected to the housing 10w. The gas introduction portion 60i is, for example, a mouth piece. As the gas introduction portion 60i, a cannula tube or the like may be used. As the gas introduction portion 60i, a mask may be used.

In the housing 10w, a first pipe 61p is provided. One end of the first pipe 61p is connected to the gas introduction portion 60i. The other end of the first pipe 61p is connected to an external environment. In this example, on an inlet side of the first pipe 61p, a flow rate meter 61fm is provided. The flow rate meter 61fm is connected to the gas introduction portion 60i. On an outlet side of the first pipe 61p, a one-way valve 61dv is provided. A part of the sample gas 50 introduced from the gas introduction portion 60i is released to the external environment through the one-way valve 61dv.

To the first pipe 61p, a second pipe 62p is connected. One end of the second pipe 62p is connected to the first pipe 61p. The other end of the second pipe 62p is connected to the cell portion 20. In this example, on the route of the second pipe 62p, a dehumidification portion 62f is provided. As the dehumidification portion 62f, for example, a filter or the like which adsorbs water is used. Between the first pipe 61p and the cell portion 20, a first solenoid valve V1 is provided. In this example, between the first solenoid valve V1 and the dehumidification portion 62f, a needle valve 62nv is provided. In this example, between the first solenoid valve V1 and the cell portion 20, a spiral tube 62s is provided. The spiral tube 62s may be omitted. The needle valve 62nv is provided as needed and may be omitted.

In the cell portion 20, for example, a heater 28 may be provided. In the cell portion 20, a pressure meter 27 may be provided.

To a portion between the first solenoid valve V1 and the spiral tube 62s, one end of a third pipe 63p is connected. The other end of the third pipe 63p is connected to a one-way valve 63dv. Through the third pipe 63p, air can be introduced into the cell portion 20 from the external environment. In the third pipe 63p, a third solenoid valve V3 is provided. Between the third solenoid valve V3 and the one-way valve 63dv, a $CO_2$ filter is provided. A $CO_2$ filter 63f reduces the amount of carbon dioxide in the air introduced from the external environment. In this example, between the third solenoid valve V3 and the $CO_2$ filter 63f, a needle valve 63nv is provided. The air is introduced from the external environment through the one-way valve 63dv. By passing through the $CO_2$ filter, $CO_2$ is removed from the air. The air from which $CO_2$ is removed can be introduced into the cell portion 20 by passing through the third solenoid valve V3. The needle valve 63nv is provided as needed and may be omitted.

By the operation of the solenoid valve, the sample gas 50 is introduced into the cell portion 20 through the second pipe 62p. Alternatively, the air from which $CO_2$ is removed is introduced into the cell portion 20 through third pipe 63p.

On an outlet side of the cell portion 20, one end of a fourth pipe 64p is connected. The other end of the fourth pipe 64p is connected to the external environment (outside the housing 10w). In this example, a second solenoid valve V2 is provided in the fourth pipe 64p. Between the second solenoid valve V2 and the external environment, an exhaust portion 65 (a pump, a fan, or the like) is provided. In this example, between the exhaust portion 65 and the second solenoid valve V2, a needle valve 64nv is provided. The needle valve 64nv is provided as needed and may be omitted.

That is, a part of the sample gas 50 introduced from the gas introduction portion 60i is introduced into the cell portion 20 through the second pipe 62p. The first carbon dioxide 51 and the second carbon dioxide 52 in this gas (breath 50a) are detected in the cell portion 20.

Another part (a large part) of the sample gas 50 introduced from the gas introduction portion 60i is released to the external environment through the first pipe 61p. That is, the amount (flow rate) of the sample gas 50 flowing through the first pipe 61p is larger than the amount (flow rate) of the sample gas 50 flowing through the second pipe 62p. According to this, when the sample gas 50 is collected, a test subject (person) is prevented from feeling suffocated.

By using the flow rate meter 61*fm*, a state of introduction of the sample gas 50 is detected. Based on this detection result, a detection operation is performed. That is, the start of introduction of the sample gas 50 becomes clear, and the precision of detection is improved.

By using the needle valve 62*nv*, the flow rate inside the second pipe 62*p* is restricted, and thus, it becomes possible to stably supply the sample gas 50.

By bringing the first solenoid valve V1 to an open state, the sample gas 50 is introduced into the cell portion 20. While detecting the first carbon dioxide 51 and the second carbon dioxide 52 in the sample gas 50 introduced into the cell portion 20 (that is, during the sample data measurement period Ps1), the first solenoid valve V1 and the second solenoid valve V2 are brought to a closed state. By doing this, the state of the gas in the cell portion 20 is stabilized, and the operation of the detection is enhanced. In the sample data measurement period Ps1, the third solenoid valve V3 is in a closed state.

The temperature of the sample gas 50 to be introduced into the cell portion 20 is preferably constant. By using the spiral tube 62*s* and a heater or the like, the temperature of the sample gas 50 to be introduced into the cell portion 20 can be controlled with high precision. The temperature is, for example, about 40° C.

The third solenoid valve V3 is brought to an open state, and by the operation of the second solenoid valve V2, the needle valve 64*nv*, and the exhaust portion 65, the gas in the cell portion 20 is released to the external environment.

When the detection operation is performed in a state where the sample gas 50 is not introduced into the cell portion 20 (that is, during the reference data measurement period Pr1), the first solenoid valve V1 is brought to a closed state and the third solenoid valve V3 is brought to an open state. By doing this, air from the external environment (air from which $CO_2$ is removed) is introduced into the cell portion 20.

Figure 7:
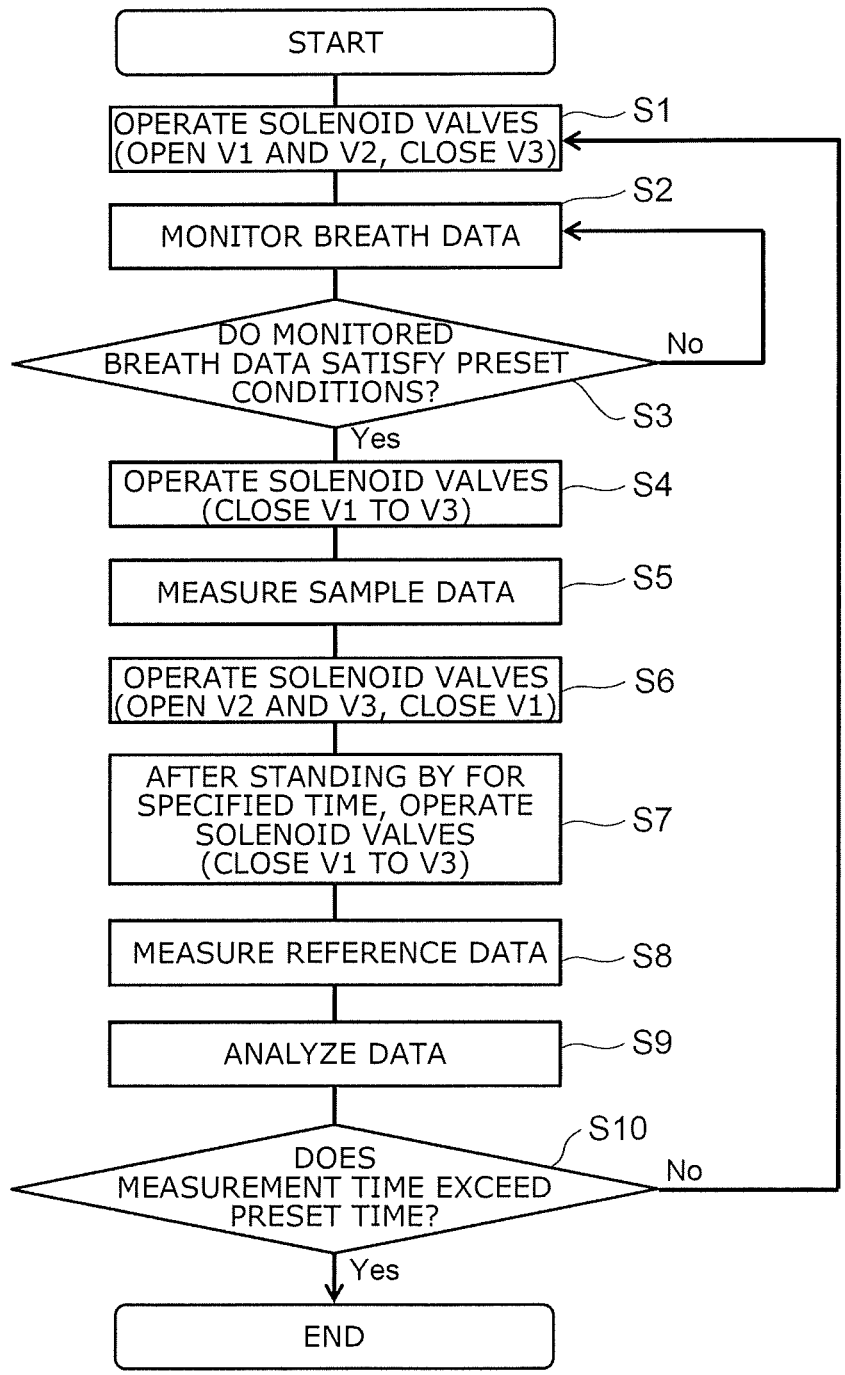
FIG. 7 is a schematic view illustrating the operation of the breath diagnostic apparatus according to the first embodiment.

FIG. 7 is a schematic view illustrating the operation of the breath diagnostic apparatus according to the first embodiment.

As shown in FIG. 7, the measurement is started.

First, the solenoid valves are operated (Step S1). Specifically, the second solenoid valve V2 and the third solenoid valve V3 are brought to an open state and the first solenoid valve V1 is brought to a closed state.

After standing by for a specified time, the solenoid valves are operated (Step S2). Specifically, the first solenoid valve V1, the second solenoid valve V2, and the third solenoid valve V3 are brought to a closed state.

Reference data are measured (Step S3).

Thereafter, the solenoid valves are operated (Step S4). Specifically, the first solenoid valve V1 and the second solenoid valve V2 are brought to an open state, and the third solenoid valve V3 is brought to a closed state.

The flow rate meter data are monitored (Step S5).

It is determined whether or not the output value of the flow rate meter exceeds a preset value (for example, a previously set value) (Step S6). In Step S6, when the output value of the flow rate meter does not exceed the preset value, the operation returns to Step 5. In Step S6, when the output value of the flow rate meter exceeds the preset value, the following Step S7 is performed.

That is, the solenoid valves are operated (Step S7). Specifically, the first solenoid valve V1, the second solenoid valve V2, and the third solenoid valve V3 are brought to a closed state.

Thereafter, sample data are measured (Step S8). Then, the data are analyzed (Step S9).

It is determined whether or not the measurement time exceeds a preset time (S10). In Step S10, when the measurement time does not exceed the preset time, the operation returns to Step S1. In Step S10, when the measurement time exceeds the preset time, the measurement is finished. The above-mentioned Steps S1 to S9 correspond to one measurement period Pm1.

Second Embodiment

Figure 8:
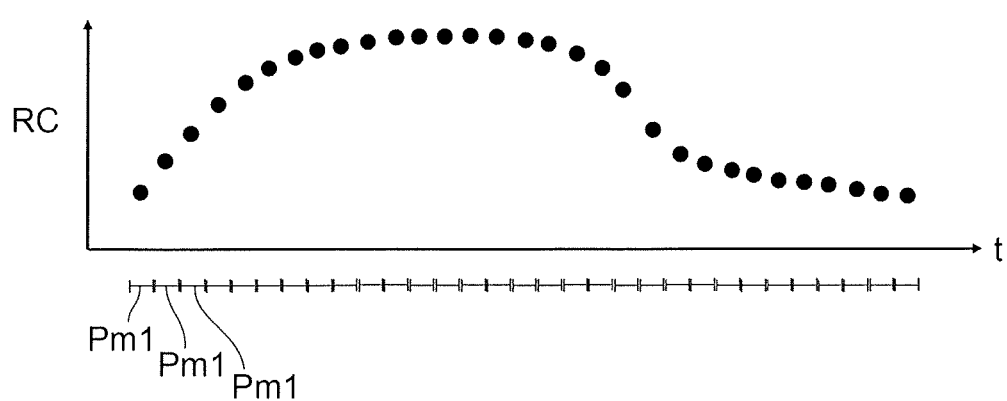
FIG. 8 is a schematic view illustrating an operation of a breath diagnostic apparatus according to a second embodiment.

FIG. 8 is a schematic view illustrating an operation of a breath diagnostic apparatus according to a second embodiment.

As shown in FIG. 8, in the embodiment, the operation in the measurement period Pm1 is performed a plurality of times continuously. That is, Steps S1 to S9 described with reference to FIG. 7 are performed a plurality of times.

In one measurement period Pm1, a ratio of the amount of the second carbon dioxide 52 to the amount of the first carbon dioxide 51 is calculated. By continuously providing the measurement period Pm1 a plurality of times and continuously performing the measurement, a change over time in the amount of the second carbon dioxide 52 is known. That is, the control portion 45 performs calculation of the ratio a plurality of times.

For example, a change over time in the relative ratio of $^{13}CO_2$ to $^{12}CO_2$ contained in the breath 50*a* can be measured. For example, the gastric clearance and the relative amount of $^{13}CO_2$ have a relation with each other. Based on the measurement result of the change over time in the relative ratio of $^{13}CO_2$ to $^{12}CO_2$, the diagnosis of gastric clearance can be made.

When a person takes a labeled compound with enriched $^{13}C$ ($^{13}C$-labeled compound), diagnosis of health conditions of the person can be made. For example, a person takes $^{13}C$-urea as the $^{13}C$-labeled compound. At this time, when *Helicobacter pylori* is present, the relative amount of $^{13}CO_2$ increases. On the other hand, for example, a person takes $^{13}C$-acetate as the $^{13}C$-labeled compound. By evaluating the breath 50*a* at this time, diagnosis can be made with respect to gastric clearance. In the case where $^{13}C$-acetate is taken, the gastric clearance and the relative amount of $^{13}CO_2$ have a relation with each other.

FIGS. 9A to 9B are schematic views illustrating a part of the breath diagnostic apparatus according to the embodiment.

FIG. 9A is a schematic perspective view. FIG. 9B is a cross-sectional view taken along the line A1-A2 of FIG. 9A. FIG. 9C is a schematic view illustrating the operation of a light source portion 30.

In this example, as the light source portion 30, a semiconductor light-emitting element 30*a*L is used. As the semiconductor light-emitting element 30*a*L, a laser is used. In this example, a quantum cascade laser is used.

As shown in FIG. 9A, the semiconductor light-emitting element 30*a*L includes a substrate 35, a stacked body 31, a first electrode 34*a*, a second electrode 34*b*, a dielectric layer 32 (first dielectric layer), and an insulating layer 33 (second dielectric layer).

Between the first electrode 34*a* and the second electrode 34*b*, the substrate 35 is provided. The substrate 35 includes a first portion 35*a*, a second portion 35*b*, and a third portion 35*c*. These portions are disposed in the same one plane. This plane crosses (for example, is parallel) in a direction from the first electrode 34a to the second electrode 34b. Between the first portion 35a and the second portion 35b, the third portion 35c is disposed.

Between the third portion 35c and the first electrode 34a, the stacked body 31 is provided. Between the first portion 35a and the first electrode 34a, and between the second portion 35b and the first electrode 34a, the dielectric layer 32 is provided. Between the dielectric layer 32 and the first electrode 34a, the insulating layer 33 is provided.

The stacked body 31 has a stripe shape. The stacked body 31 functions as a ridge waveguard RG. Two end faces of the ridge waveguide RG become mirror faces. Light 31L emitted in the stacked body 31 is emitted from the end face (light emission face). The light 31L is infrared laser light. An optical axis 31Lx of the light 31L is along an extending direction of the ridge waveguide RG.

As shown in FIG. 9B, the stacked body 31 includes, for example, a first clad layer 31a, a first guide layer 31b, an active layer 31c, a second guide layer 31d, and a second clad layer 31e. These layers are arranged in this order along a direction from the substrate 35 to the first electrode 34a. Each of the refractive index of the first clad layer 31a and the refractive index of the second clad layer 31e is lower than each of the refractive index of the first guide layer 31b, the refractive index of the active layer 31c, and the refractive index of the second guide layer 31d. The light 31L generated in the active layer 31c is confined in the stacked body 31. The first guide layer 31b and the first clad layer 31a are sometimes combined and called "clad layer". The second guide layer 31d and the second clad layer 31e are sometimes combined and called "clad layer".

The stacked body 31 has a first side surface 31sa and a second side surface 31sb perpendicular to the optical axis 31Lx. A distance 31w (width) between the first side surface 31sa and the second side surface 31sb is, for example, 5 μm or more and 20 μm or less. According to this, for example, the control in a horizontal transverse mode is facilitated, and the improvement of output is facilitated. When the distance 31w is excessively long, a higher-order mode is likely to occur in a horizontal transverse mode, and it is difficult to increase the output.

The refractive index of the dielectric layer 32 is lower than the refractive index of the active layer 31c. According to this, the ridge waveguide RG is formed along the optical axis 31Lx by the dielectric layer 32.

As shown in FIG. 9C, the active layer 31c has, for example, a cascade structure. In the cascade structure, for example, a first region r1 and a second region r2 are alternately stacked. A unit structure r3 includes the first region r1 and the second region r2. A plurality of unit structures r3 is provided.

For example, in the first region r1, a first barrier layer BL1 and a first quantum well layer WL1 are provided. In the second region r2, a second barrier layer BL2 is provided. For example, in another first region r1a, a third barrier layer BL3 and a second quantum well layer WL2 are provided. In another second region r2a, a fourth barrier layer BL4 is provided.

In the first region r1, intersubband optical transition in the first quantum well layer WL1 occurs. Due to this, for example, light 31La having a wavelength of, for example, 3 μm or more and 18 μm or less is emitted.

In the second region r2, energy of a carrier c1 (for example, an electron) injected from the first region r1 can be relaxed.

In the quantum well layer (for example, the first quantum well layer WL1), a well width WLt is, for example, 5 nm or less. When the well width WLt is narrow in this manner, an energy level is discrete, and for example, a first subband WLa (a high level Lu) and a second subband WLb (a low level LI), or the like occur. The carrier c1 injected from the first barrier layer BL1 is effectively confined in the first quantum well layer WL1.

When the transition of the carrier c1 from a high level Lu to a low level LI occurs, the light 31La corresponding to the difference in energy (the difference between the high level Lu and the low level LI) is emitted. That is, optical transition occurs.

Similarly, in the second quantum well layer WL2 in another first region r1a, light 31Lb is emitted.

In the embodiment, the quantum well layer may include a plurality of wells whose wave functions overlap each other. The high levels Lu of the respective plurality of quantum well layers may be the same as each other. The low levels LI of the respective plurality of quantum well layers may be the same as each other.

For example, intersubband optical transition occurs in either of a conduction band and a valence band. For example, recombination of a hole and an electron by p-n junction is not needed. For example, optical transition occurs by the carrier c1 of either of a hole and an electron, and light is emitted.

In the active layer 31c, for example, by a voltage applied between the first electrode 34a and the second electrode 34b, the carrier c1 (for example, an electron) is injected into the quantum well layer (for example, the first quantum well layer WL1) through the barrier layer (for example, the first barrier layer BL1). According to this, intersubband optical transition occurs.

The second region r2 has, for example, a plurality of subbands. The subband is, for example, a miniband. The difference in energy in the subbands is small. It is preferred that the subbands are close to continuous energy bands. As a result, the energy of the carrier c1 (electron) is relaxed.

In the second region r2, for example, light (for example, infrared light having a wavelength of 3 μm or more and 18 μm or less) is substantially not emitted. The carrier c1 (electron) at a low level LI in the first region r1 passes through the second barrier layer BL2 and is injected into the second region r2 and relaxed. The carrier c1 is injected into another first region r1a connected in cascade. In this first region r1a, optical transition occurs.

In the cascade structure, optical transition occurs in each of the plurality of unit structures r3. According to this, it becomes easy to obtain a high light output in the entire active layer 31c.

In this manner, the light source portion 30 includes the semiconductor light-emitting element 30aL. The semiconductor light-emitting element 30aL emits the measurement light 30L by energy relaxation of electrons in the subbands in the plurality of quantum wells (for example, the first quantum well layer WL1 and the second quantum well layer WL2, etc.).

In the quantum well layers (for example, the first quantum well layer WL1 and the second quantum well layer WL2, etc.), for example, InGaAs is used. For example, in the barrier layers (for example, the first to fourth barrier layers BL1 to BL4, etc.), for example, InAlAs is used. At this time, for example, when InP is used as the substrate 35, favorable lattice matching is obtained in the quantum well layers and the barrier layers.

The first clad layer 31a and the second clad layer 31e contain, for example, Si as an n-type impurity. The concentration of the impurity in these layers is, for example, $1 \times 10^{18}$ cm$^{-3}$ or more and $1 \times 10^{20}$ cm$^{-3}$ or less (for example, about $6 \times 10^{18}$ cm$^{-3}$). The thickness of each of these layers is, for example, 0.5 µm or more and 2 µm or less (for example, about 1 µm).

The first guide layer 31b and the second guide layer 31d contain, for example, Si as an n-type impurity. The concentration of the impurity in these layers is, for example, $1 \times 10^{16}$ cm$^{-3}$ or more and $1 \times 10^{17}$ cm$^{-3}$ or less (for example, about $4 \times 10^{16}$ cm$^{-3}$). The thickness of each of these layers is, for example, 2 µm or more and 5 µm or less (for example, about 3.5 µm).

The distance 31w (the width of the stacked body 31, that is, the width of the active layer 31c) is, for example, 5 µm or more and 20 µm or less (for example, about 14 µm).

The length of the ridge waveguide RG is, for example, 1 mm or more and 5 mm or less (for example, about 3 mm). The semiconductor light-emitting element 30aL operates at an operation voltage of, for example, 10 V or less. The current consumption is lower than a carbon dioxide gas laser apparatus or the like. According to this, an operation with low power consumption can be achieved.

According to the embodiment, a high-precision gas measuring apparatus can be provided. The gas measuring apparatus includes a breath diagnostic apparatus.

Hereinabove, exemplary embodiments of the invention are described with reference to specific examples. However, the embodiments of the invention are not limited to these specific examples. For example, one skilled in the art may similarly practice the invention by appropriately selecting configurations of components included in the breath diagnostic apparatus such as the cell portion, the light source portion, the detection portion and the control portion, etc., from known art. Such practice is included in the scope of the invention to the extent that similar effects thereto are obtained.

Furthermore, any two or more components of the specific examples may be combined within the extent that the purport of the invention is included.

Moreover, all breath diagnostic apparatus practicable by an appropriate design modification by one skilled in the art based on the breath diagnostic apparatus described above as embodiments of the invention also are within the scope of the invention to the extent that the purport of the invention in included.

Various other variations and modifications can be conceived by those skilled in the art within the spirit of the invention, and it is under stood that such variations and modifications are also encompassed within the scope of the invention.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the invention.

What is claimed is:

1. A gas measuring apparatus, comprising:
   a cell portion that includes a space into which a sample gas containing a first isotope of carbon dioxide and a second isotope of carbon dioxide is introduced;
   a light source portion that emits light into the space in a wavelength band of 4.345 µm or more and 4.384 µm or less, the wavelength band including at least a first wavelength corresponding to one of absorption peak of the first isotope, a second wavelength corresponding to one of absorption peak of the second isotope, and a third wavelength corresponding to absorption peak of the first isotope or the second isotope, absorption of the first isotope at the second wavelength not corresponding to absorption peak and being lower than absorption of the second isotope;
   a detection portion that measures a first intensity of the light passing through the space into which the sample gas is introduced and a second intensity of the light passing through the space into which the sample gas is not introduced; and
   a control portion that calculates a ratio of an amount of the second isotope to an amount of the first isotope in the sample gas based on the first intensity and the second intensity,
   a range of wavenumber band of the light being 1 cm$^{-1}$ or less, and
   wavenumber of the light being swept in the range.

2. The apparatus according to claim 1, wherein
   the light source portion includes
   a semiconductor light-emitting element that emits the light by energy relaxation of electrons in subbands in a plurality of quantum wells, and
   a driving portion that sweeps the wavenumber of the light.

3. The apparatus according to claim 1, wherein the control portion calculates the ratio a plurality of times.

4. The apparatus according to claim 1,
   further comprising:
   a gas introduction portion from which the sample gas is introduced;
   a first pipe; and
   a second pipe,
   one end of the first pipe being connected to the gas introduction portion, the other end of the first pipe being connected to an external environment,
   one end of the second pipe being connected to the first pipe or the gas introduction portion, and
   the other end of the second pipe being connected to the cell portion.

5. The apparatus according to claim 4, wherein an amount of the sample gas flowing through the first pipe is larger than an amount of the sample gas flowing through the second pipe.

6. The apparatus according to claim 4,
   further comprising:
   a third pipe thorough which air is introduced into the cell portion from the external environment,
   the third pipe including a filter that reduces an amount of carbon dioxide in the air introduced from the external environment.

7. The apparatus according to claim 1, wherein the detection portion includes a semiconductor sensor element.

* * * * *